United States Patent [19]

Olinger et al.

[11] Patent Number: 5,651,988
[45] Date of Patent: Jul. 29, 1997

[54] COMBINATION OSMOTIC AND BULK FORMING LAXATIVES

[75] Inventors: Philip M. Olinger, St. Charles, Ill.; Julita Pearson, West Wickham; David Saunders, Guildford, both of United Kingdom

[73] Assignee: Xyrofin Oy, Helsinki, Finland

[21] Appl. No.: 516,769

[22] Filed: Aug. 18, 1995

[51] Int. Cl.$^6$ .............. A61K 9/14; A61K 9/16; A61K 9/20

[52] U.S. Cl. .............. 424/489; 424/195.1; 424/441; 424/464; 424/470; 424/499; 426/93; 426/103; 426/531; 514/892

[58] Field of Search .............. 424/489, 499, 424/470, 464, 441, 195.1; 426/93, 103, 531; 514/892

[56] References Cited

U.S. PATENT DOCUMENTS

| | | | |
|---|---|---|---|
| 4,321,263 | 3/1982 | Powell et al. | 424/195.1 |
| 4,459,280 | 7/1984 | Colliopoulos et al. | 424/195.1 |
| 4,548,806 | 10/1985 | Colliopoulos et al. | 424/195.1 |
| 4,714,620 | 12/1987 | Bunick et al. | 426/572 |
| 4,766,004 | 8/1988 | Moskowitz | 426/658 |
| 4,824,681 | 4/1989 | Schobel et al. | 426/103 |
| 4,882,152 | 11/1989 | Yang et al. | 424/440 |
| 4,882,160 | 11/1989 | Yang et al. | 424/440 |
| 4,911,937 | 3/1990 | Crosello et al. | 426/103 |
| 4,931,554 | 6/1990 | Bijl et al. | 514/892 |
| 4,950,140 | 8/1990 | Pflaumer et al. | 424/439 |
| 4,973,486 | 11/1990 | Matsumoto et al. | 426/548 |
| 4,978,529 | 12/1990 | Denick, Jr. | 424/195.1 |
| 4,996,051 | 2/1991 | Meer et al. | 424/195.1 |
| 4,999,200 | 3/1991 | Casillan | 424/480 |
| 5,009,916 | 4/1991 | Colliopoulos | 426/615 |
| 5,095,008 | 3/1992 | Pflaumer et al. | 514/23 |
| 5,126,150 | 6/1992 | Piatt et al. | 426/94 |
| 5,143,728 | 9/1992 | Cappel et al. | 424/195.1 |
| 5,149,541 | 9/1992 | Leis, Jr. et al. | 424/489 |
| 5,173,296 | 12/1992 | Andre et al. | 424/195.1 |
| 5,219,570 | 6/1993 | Barbera | 424/195.1 |
| 5,232,698 | 8/1993 | Hord | 424/195.1 |
| 5,232,699 | 8/1993 | Colliopoulos | 424/195.1 |
| 5,258,181 | 11/1993 | Cregier et al. | 424/195.1 |
| 5,292,518 | 3/1994 | Kuhrts | 424/439 |
| 5,320,847 | 6/1994 | Valentine et al. | 424/439 |
| 5,338,549 | 8/1994 | Hord et al. | 424/439 |
| 5,340,580 | 8/1994 | Barbera | 424/189.1 |
| 5,445,826 | 8/1995 | Kuhrts | 424/451 |
| 5,466,469 | 11/1995 | Kuhrts | 424/451 |

OTHER PUBLICATIONS

Supplementary Drugs and Other Substances, pp. 1582, 1092–1093.

*Lactitol, a new hydrogenated lactose derivative: intestinal absorption and laxative threshold in normal human subjects;* British Journal of Nutrition (1987) 57, 195–199; Patil, Grimble and Silk.

*Monitoring Bowel Habit in elderly People;* Research in the Nursing Care of Elderly People, 1987, K. Elizabeth Barnes, pp. 27–45.

*Assimilation of lactitol, an "unabsorbed" disaccharide in the normal human colon;* 1988, G K Grimble, D H Patil, and D B A Silk, pp. 1666–1671.

*Chronische funktionelle Obstipation;* Opstipation; Hammer and Ravelli; pp. S02–S08.

Primary Examiner—Amy Hulina
Attorney, Agent, or Firm—Baker & McKenzie

[57] ABSTRACT

A combination bulk-forming and osmotic laxative is provided by combining a bulk-forming laxative in the form of psyllium hydrophilic mucilloid with an osmotic laxative such as lactitol. The addition of the osmotic laxative to the bulk-forming laxative with a binder solution and subsequent drying produces an improved laxative in granulate form which is directly compressible into tablets.

27 Claims, No Drawings

1

COMBINATION OSMOTIC AND BULK FORMING LAXATIVES

FIELD OF THE INVENTION

The present invention relates generally to laxatives. Particularly, the present invention relates to a combination laxative which includes an osmotic laxative and a bulk-forming laxative. Still more particularly, the present invention relates to the granulated combination of an osmotic laxative in the form of a sugar alcohol, such as lactitol, with a bulk forming laxative such as psyllium to provide a laxative form which is directly compressible.

BACKGROUND AND SUMMARY OF THE INVENTION

There are four general types of laxatives that are currently available: 1) bulk-forming; 2) osmotic; 3) stimulatory; 4) softening agents. The present application is directed toward the bulk-forming and osmotic types and specifically towards the use of an osmotic laxative in enhancing and correcting deficiencies found in bulk-forming laxatives.

While bulk-forming laxatives such as those formed from psyllium husks provide generally safe and effective laxatives, psyllium laxatives generally suffer from three primary deficiencies. First, bulk-forming laxatives such as psyllium are not directly compressible and lack the ability to be readily formulated in tabletted form. Second, they do not disperse well and often form lumps of psyllium material, the interiors of which are still substantially dry. Third, psyllium seed husk has very poor wetting qualities and therefore does not mix well.

The present invention addresses the poor compressibility of psyllium husk by combining the ground psyllium husk with a sugar alcohol, such as lactitol, which, as an osmotic laxative, has its own laxative properties.

Specifically, psyllium hydrophilic mucilloid has not yet successfully been provided in a tablet form but only in a powder form that may be dispersed in water. A chewable tablet containing psyllium would be beneficial because the masticating action in the mouth would aid dispersion. The present invention combines psyllium, which is not directly compressible, with a sugar alcohol to form a compressible granulate which may be compressed into tablets. Thus, the present invention provides a solution to problems inherent with one laxative—bulk-forming laxatives such as psyllium seed husks—by combining the bulk-forming laxative with another laxative—an osmotic laxative, such as lactitol.

By way of background, bulk-forming laxatives rely upon the use of dietary fiber. Dietary fiber is the portion of plant materials that is resistant to digestion. There are generally two types of dietary fiber: insoluble and soluble. Insoluble dietary fiber passes through the digestive system in a substantially intact form. Insoluble fiber passes through the digestive system quickly because it does not absorb water, like soluble fiber.

In contrast, soluble fiber absorbs water in the small intestine and in the stomach. Psyllium is one source of soluble fiber. Specifically, the psyllium form known as psyllium hydrophilic mucilloid consists of the husk (either milled or unmilled) of blond psyllium seeds. When exposed to water in the stomach and small intestine, the psyllium hydrophilic mucilloid forms a gelatinous mass which aids in the treatment of constipation by acting as a fecal softening agent and also acts to soothe and protect the small intestine.

However, obtaining an appropriate gelatinous mass of psyllium hydrophilic mucilloid in the small intestine is problematic due to the poor dispersability and mixability of the psyllium hydrophilic mucilloid in water prior to ingestion. The individual particles of the psyllium hydrophilic mucilloid tend to lump or agglomerate together when mixed with water. The psyllium hydrophilic mucilloid often fails to evenly disperse throughout the gelatinous mass and the hydration of psyllium hydrophilic mucilloid tends to take place over the exterior surface of such an agglomerated mass to form gelatin-coated lumps, the interiors of which are substantially dry. These gelatin-coated lumps are less voluminous than properly dispersed psyllium hydrophilic mucilloid and therefore the laxative benefits of the psyllium are compromised.

The poor dispersability of psyllium hydrophilic mucilloid is exacerbated by its poor mixing characteristics. Psyllium hydrophilic mucilloid is difficult to wet and tends to float on the surface of water. When mixing with water is attempted, the psyllium hydrophilic mucilloid forms lumps or masses. Psyllium is also difficult to mix when combined in the batter of a baked or continuously extruded food. Often, lumps of psyllium and material will result which result in an unacceptable food product due to textural deficiencies or to the poor taste of the psyllium material and psyllium derivatives.

In contrast to bulk-forming laxatives, osmotic laxatives act to retain water in the colonic lumen thereby counteracting the normal dehydrating action of the colon. By suppressing the dehydration action of the colon, the osmotic laxative produces a fecal stream which is softer, bulkier and easier to expel.

Lactitol may be used as an osmotic laxative because it is not absorbed in the small intestine and is thereafter hydrolysed and fermented in the large bowel by the action of intestinal microflora resulting in the liberation of galactose and sorbitol which are thereafter metabolized to organic acids and short chain fatty acids by colonic anaerobes. An osmotic effect is created in the colon, which normally acts to hydrate the fecal stream. The reduction in the dehydrating action of the colon produces a softer, bulkier fecal stream. Studies have shown that administration of 10 to 20 grams of lactitol daily results in a predictable laxation response of typically 24 hours or less. In contrast, other sugar alcohols have not proven to be effective osmotic laxatives and are therefore not recognized as such because they are unpredictable and not necessarily dose-dependent.

Additionally, lactitol exhibits other properties which makes it a preferred candidate for combination with psyllium. Specifically, lactitol does not induce an increase in blood glucose or insulin levels and contributes half the calories of most other carbohydrates (2 calories per gram). Because the control of blood glucose, lipids and body weight are primary goals in diabetes management, lactitol is considered to be a beneficial product for diabetics. Lactitol is also non-cariogenic and has a moderate, sugar-like sweetness. Lactitol also has good solubility, low hygroscopicity, and when provided in a crystalline form, is suitable for dry mixing. Finally, lactitol is also available at a price that is competitive with other sugar alcohols.

Thus, the two types of laxatives discussed above, bulk-forming and osmotic, operate by two entirely different mechanisms. Bulk-forming laxatives absorb water and expand in the colonic lumen; in contrast, osmotic laxatives retain water in the colonic lumen by osmosis.

While the prior art teaches the use of both types of laxatives and further teaches the use of psyllium as a bulk-forming laxative and the use of lactitol as an osmotic laxative, the prior art does not teach a combination of psyllium and lactitol. Further, the prior art does not teach the use of an osmotic laxative, such as lactitol, to enhance the compressibility, dispersability and mixability of bulk-forming laxatives, such as psyllium. One prior combination of psyllium and a sugar alcohol, specifically mannitol, is taught in U.S. Pat. No. 5,320,847 to Valentine et al. However, Valentine teaches the use of mannitol only as a low-calorie sweetener or substitute for free sugar, not as an osmotic laxative. Mannitol is not proven or recognized as a therapeutic osmotic laxative. Valentine also does not attempt to provide a psyllium laxative in a tablet form.

A laxative provided in tablet form could be designed either for immediate swallowing or chewing. As noted above, psyllium is not available in tablet form because it is simply not compressible. However, when combined with a sugar alcohol, such as lactitol, psyllium can be provided in a tablet form due to the sufficient compressibility of the psyllium/lactitol combination. The masticating action of the mouth aids in the dispersion of the psyllium. Providing psyllium in a tablet form also provides a vehicle whereby other ingredients, such as medications, minerals and vitamins can be delivered with the laxative material. Finally, tablets are easily transported by the consumer and easily dispensed by the pharmacist.

Two criteria are used to evaluate the quality of a tablet. Those two criteria are crushing strength or hardness and friability. Hardness is a measure of a tablet's strength. Hardness is measured by determining the lateral breaking strength expressed in kilograms, Strong Cobb Units (S.C.U.) or Newtons (N) exerted on a single tablet at the moment of rupture. Typical hardness testers are manufactured by Key Instruments. In the context of chewable tablets, the tablet hardness must be greater than about 30N to be commercially useful.

On the other hand, friability is another measure of a tablet's ability to resist chipping and breaking during shipment and handling. Friability is measured under standard conditions by weighing out a certain number of tablets (generally 20 or more) and placing them in a rotating plexiglass drum in which they are lifted during replicate revolutions by a radial louver and then dropped through the diameter of the drum. The tablets are then re-weighed and a percentage of the powder that has rubbed off is calculated. Friability of less than about 10% is considered to be acceptable for most chewable tablet contexts.

It is therefore an object of the present invention to provide an improved laxative by combining a bulk-forming laxative with an osmotic laxative.

Yet another object of the present invention is to provide an improved psyllium bulk-forming laxative by combining psyllium with an osmotic laxative.

Another object of the present invention is to provide an improved bulk-forming laxative/osmotic laxative combination which may be provided in tablet form or powder form.

It is still another object of the present invention to improve the compressibility, dispersability and mixability of psyllium husk powder by combining the psyllium husk powder with lactitol.

Yet another object of the present invention is to provide a means for producing a compressible psyllium/lactitol granulate using fluid bed granulation techniques.

Other objects and advantages of the invention will become apparent upon reading the summary, description of the preferred embodiments and the appended claims.

The above and other objects are accomplished by the present invention in which it has been discovered that a combination of lactitol as an osmotic laxative and psyllium as a bulk-forming laxative. The combination of the present invention results in an improved laxative with the qualities of both an osmotic laxative and an enhanced bulk-forming laxative due to the enhanced compressibility, dispersability and mixability of the psyllium.

One preferred embodiment involves the combination of psyllium hydrophilic mucilloid and lactitol. Specifically, approximately equal parts of psyllium hydrophilic mucilloid and lactitol are dry blended. The resulting powder mixture may be mixed with water and taken orally. Further, a binder solution may be subsequently mixed with the psyllium and lactitol to produce a granulate. The granulate may thereafter be dried and compressed into tablets.

If the granulate is to be compressed into tablets, the preferred form of lactitol is lactitol monohydrate. Three known binder solutions are available, including 60% lactitol solution, 3% polyvinylpyrrolidone (PVP) solution and 10% gelatin (250 Bloom) solution. The addition of 10% by weight microcrystalline cellulose has been found to improve the hardness and friability of the tablets.

If the resulting lactitol psyllium mixture is to be provided in a powder form, three known forms of lactitol are available. Specifically, the lactitol may be provided in the form of anhydrous lactitol crystals, lactitol monohydrate or anhydrous lactitol. It is preferred that the lactitol monohydrate and anhydrous lactitol monohydrate be milled to a maximum particle size of 125 microns or less. The preferred form of psyllium is Roeper (60 mesh).

The present invention may also be provided in the form of a baked product, such as a cookie, cracker or cake.

DESCRIPTION OF THE PREFERRED EMBODIMENTS

The present invention is provided in two forms: powdered and granulate. The granulate may either be dispersed in water prior to ingestion or may be directly compressed into a tablet form. The preferred granulate form of the present invention includes a dry blend of approximately equal parts of psyllium powder and lactitol. A liquid binder solution is then added and the psyllium, lactitol and binder solution is mixed and dried. The preparation is then compressed into tablet form. The following examples are provided.

EXAMPLES 1-4

100 grams of lactitol monohydrate was dry-blended with 100 grams of psyllium powder. 64 grams of a 60% lactitol solution (w/w) was added to the dry mixture and the three components were mixed continuously until thoroughly wetted. 1% magnesium stearate was added as a tabletting lubricant. The blend was then dried overnight at 60° C. and passed through a 1000 micron sieve to yield a granulate. The granulate was blended with 1% magnesium stearate (w/w) and tablets were prepared on a Manesty 2C single punch press using a 15 mm diameter beveled edge flat faced punch. The compression setting was increased until an acceptable tablet was obtained. The tablet hardness or crushing strength was measured using a Key Instruments tablet hardness tester. An average of 10 samples were taken. The friability of the tablets was measured using a rotary friability tester. Ten tablets were dropped 100 times with the weight loss being recorded. The following results were obtained:

|  | Exh. 1 |
|---|---|
| Average weight | 1.051 g |
| Average thickness | 4.7337 mm |
| Average hardness | 31 N |
| Average friability | 47.4% |

The granulate of Example 1 was also combined with 10% by weight of microcrystalline cellulose (MCC) prior to tabletting. As seen below, the addition of MCC increased tablet hardness and decreased tablet friability.

|  | Exh. 2 |
|---|---|
| Average weight | 1.0624 g |
| Average thickness | 4.7651 mm |
| Average hardness | 38 N |
| Average friability | 7.6% |

Examples 3 and 4 include the same composition as that shown in Example 1, i.e., without the addition of microcrystalline cellulose. The following results were obtained:

|  | Ex. 3 | Ex. 4 |
|---|---|---|
| Average weight | 1.2049 g | 1.1944 g |
| Average thickness | 5.4505 mm | 5.4139 mm |
| Average hardness | 35 N | 31 N |

EXAMPLES 5–7

Softer tablets were obtained by using polyvinylpyrrolidone (PVP) binder solution. Examples 5, 6 and 7 are presented below which illustrate the use of PVP binder solution. Again, 100 g lactitol was dry blended with 100 g psyllium powder. 29 g 3% PVP solution was added to the dry mixture and mixed until completely wetted. The mix was dried overnight at 60° C. and sieved to obtain a suitable granulate. The granulate was blended with 1% magnesium stearate (w/w) and tabletted.

|  | Ex. 5 | Ex. 6 | Ex. 7 |
|---|---|---|---|
| Average weight | 1.0724 g | 1.0676 g | 1.0464 |
| Average thickness | 5.116 mm | 4.9942 mm | 4.8462 mm |
| Average hardness | 11 N | 16 N | 18 N |

EXAMPLES 8 AND 9

Tablets can also be formed from the mixtures bound with a gelatin binder solution. Again, 100 g lactitol and 100 g psyllium powder were dry blended. 35 g 10% gelatin (250 Bloom) solution was slowly added to the mixture and mixed until thoroughly wetted. The mix was then spread out onto a metal tray and dried overnight at 60° C. and sieved to produce a suitable granulate. The granulate was blended with 1% magnesium stearate (w/w) and tabletted. The weight, thickness and hardness properties are as follows:

|  | Ex. 8 | Ex. 9 |
|---|---|---|
| Average weight | 1.0723 g | 1.0702 g |
| Average thickness | 4.8415 mm | 4.8365 mm |
| Average hardness | 22 N | 20 N |

EXAMPLES 10–12

Approximately 100 g lactitol monohydrate which was milled and screened through a 125 micron sieve was added to 100 g psyllium powder. No binder solution was added to the mixture. The blend was mixed for 2 minutes with 1% added magnesium stearate and pressed into a tablets. The following results were obtained:

|  | Ex. 10 | Ex. 11 | Ex. 12 |
|---|---|---|---|
| Average weight | 1.1137 g | 1.1208 g | 1.1416 g |
| Average thickness | 5.3001 mm | 5.3633 mm | 5.4582 mm |
| Average hardness | 17 N | 17 N | 16 N |

EXAMPLES 13 AND 14

Using the same procedure, i.e. no binder solution, approximately 100 g milled anhydrous lactitol and 100 g psyllium powder were combined and blended with 1% magnesium stearate for 1–2 minutes before being pressed into tablet form. The following results were obtained:

|  | Ex. 13 | Ex. 14 |
|---|---|---|
| Average weight | 1.1384 g | 1.1389 g |
| Average thickness | 5.3301 mm | 5.3198 mm |
| Average hardness | 20 N | 21 N |

EXAMPLE 15

Finally, 100 g anhydrous lactitol crystals and 100 g psyllium powder were combined and blended for 1–2 minutes with 1% magnesium stearate. However, this mixture could not be compressed into tablet form and therefore must be provided to the consumer in powdered form.

Accordingly, if the product is to be provided in tablet form, a lactitol solution was found to be the superior binding solution and the addition of microcrystalline cellulose (MCC) was found to improve hardness and friability characteristics. If the product is to be provided to the consumer in powder form, the addition of a binder solution is not necessary.

Either the granulate form (Examples 1–9) or the dry mixture (Examples 10–15) can be used to manufacture laxative-containing baked goods. Two cookie recipes are as follows:

| EXHIBIT 16 | |
|---|---|
| lactitol monohydrate | 9.2% |
| lactitol/psyllium granulate (Example 1) | 35.8% |
| flour | 18.3% |
| shortening | 17.5% |
| eggs | 10.4% |
| skim milk powder | 7.5% |

-continued

| | |
|---|---|
| salt | 0.2% |
| baking soda | 0.3% |
| cream of tartar | 0.2% |
| Acesulfame K | 0.05% |
| flavor | 0.5% |

| EXHIBIT 17 | |
|---|---|
| lactitol monohydrate | 30.0% |
| psyllium | 15.0% |
| flour | 18.3% |
| shortening | 17.5% |
| eggs | 10.4% |
| skim milk powder | 7.5% |
| salt | 0.2% |
| baking soda | 0.3% |
| cream of tartar | 0.2% |
| Acesulfame K | 0.05% |
| flavor | 0.5% |

Thus, the present invention may be provided in a powder form, a granulate form, a tablet form and in a baked product. Additional components such as medications, vitamins and minerals may also be provided with the combination osmotic/bulk-forming laxative of the present invention. Intense sweeteners such as Acesulfame K and aspartame may be added to enhance the flavor of the products. Flavorings and colors may also be used. Other tabletting lubricants in addition to magnesium stearate will be apparent to those skilled in the art.

Although only 17 embodiments of the present invention have been illustrated and described, it will at once be apparent to those skilled in the art that variations may be made within the spirit and scope of the invention. Accordingly, it is intended that the scope of the invention be limited solely by the scope of the hereafter appended claims and not by any specific wording in the foregoing description.

What is claimed is:

1. A combination osmotic and bulk-forming laxative comprising:

lactitol in an amount from about 40% to about 60%, and psyllium hydrophilic mucilloid powder in an amount from about 40% to about 60%.

2. The laxative of claim 1, wherein the lactitol and psyllium hydrophilic mucilloid powder are combined by dry blending.

3. The laxative of claim 1, wherein the lactitol and psyllium hydrophilic mucilloid powder are combined in a granulate form.

4. The laxative of claim 1, wherein the lactitol is further characterized as lactitol monohydrate particles in a milled form and having a particle diameter of less than 125 microns.

5. The laxative of claim 1, wherein the lactitol is further characterized as anhydrous lactitol crystals in a milled form and having a particle size of less than 125 microns.

6. The laxative of claim 1, wherein the psyllium mucilloid powder is further characterized as having a particle size of less than 125 microns.

7. The laxative of claim 4, wherein the combination is further characterized as being a granulate which is directly compressible into tablets.

8. The laxative of claim 5, wherein the combination is further characterized as being a granulate which is directly compressible into tablets.

9. A process for producing a combination bulk-forming and osmotic laxative in granulate form, the method comprising the following steps:

dry blending approximately equal parts of psyllium hydrophilic mucilloid powder and lactitol, adding a binder solution, mixing the binder solution, psyllium hydrophilic mucilloid powder and lactitol together to form a wet granulate, drying the wet granulate to provide a dry granulate, screening the dry granulate to a desired particle size or distribution.

10. The process of claim 9, wherein the lactitol is further characterized as lactitol monohydrate particles having a diameter of essentially less than about 125 microns.

11. The process of claim 9, wherein the lactitol is further characterized as anhydrous lactitol particles having a diameter of essentially less than 125 about microns.

12. The process of claim 9, wherein the binder solution is further characterized as being aqueous lactitol (60%) solution.

13. The process of claim 9, wherein the binder solution is further characterized as being aqueous PVP (3%) solution.

14. The process of claim 9, wherein the binder solution is further characterized as being aqueous gelatin (10%) solution.

15. The process of claim 9 further comprising the following step:

compressing portions of the dried granulate into tablets.

16. A combination osmotic and bulk-forming laxative provided in tablet form, the laxative comprising:

a directly compressible granulate including lactitol and psyllium hydrophilic mucilloid, an intense sweetener, microcrystalline cellulose, a tabletting lubricant.

17. The laxative of claim 16, wherein the intense sweetener is aspartame.

18. The laxative of claim 16, wherein the intense sweetener is Acesulfame K.

19. The laxative of claim 16, wherein the directly compressible granulate is further characterized as including lactitol in an amount from about 40% to about 60% and psyllium hydrophilic mucilloid powder in an amount from about 60% to about 40%.

20. The laxative of claim 16, wherein the directly compressible granulate is present in an amount ranging from about 60% to about 90% and the microcrystalline cellulose is present in an amount ranging from about 40% to about 10%.

21. The laxative of claim 16, further comprising therapeutic amounts of vitamins.

22. The laxative of claim 16, further comprising therapeutic amounts of minerals.

23. A process for producing a combination bulk-forming and osmotic laxative in tablet form, the method comprising the following steps:

dry blending a directly compressible granulate with microcrystalline cellulose and a tabletting lubricant, the directly compressible granulate comprising psyllium hydrophilic mucilloid powder in an amount ranging from about 40% to about 60% and lactitol in an amount ranging from about 60% to about 40%, compressing the granulate to form individual tablets.

24. The process of claim 23, wherein the microcrystalline cellulose is present an amount ranging from about 40% to about 10%.

the directly compressible granulate is present in an amount ranging from about 60% to about 90%.

25. The process of claim 24 further comprising the following step between the dry blending step and compressing step:

adding in intense sweetener.

26. The process of claim 25, wherein the intense sweetener is aspartame.

27. The process of claim 25, wherein the intense sweetener is Acesulfame K.

* * * * *